US008286794B1

(12) United States Patent
Agadzi (10) Patent No.: US 8,286,794 B1
(45) Date of Patent: Oct. 16, 2012

(54) MEDICAL ORGANIZER

(76) Inventor: Victor Agadzi, Pensacola, FL (US)

( * ) Notice: Subject to any disclaimer, the term of this patent is extended or adjusted under 35 U.S.C. 154(b) by 233 days.

(21) Appl. No.: 12/925,876

(22) Filed: Nov. 2, 2010

(51) Int. Cl.
*B65D 69/00* (2006.01)
*B65D 6/00* (2006.01)

(52) U.S. Cl. ............ 206/570; 206/571; 206/225; 220/8

(58) Field of Classification Search ................ D24/128; 312/209; 248/91, 188.6, 188.5; 220/8, 495.07, 220/475; 211/88.01, 85.18, 132.1, 133.1, 211/126.6, 126.3; 206/570–572, 438, 227, 206/225; 190/109
See application file for complete search history.

(56) References Cited

U.S. PATENT DOCUMENTS

| | | | | |
|---|---|---|---|---|
| 4,141,524 A * | 2/1979 | Corvese, Jr. | .................... | 248/70 |
| 4,194,628 A * | 3/1980 | Campos | ........................ | 206/570 |
| 4,725,027 A * | 2/1988 | Bekanich | .................. | 248/125.8 |
| 5,007,688 A * | 4/1991 | Bayerlein et al. | .............. | 312/7.2 |
| 5,183,994 A * | 2/1993 | Bowles et al. | ................. | 219/387 |
| 5,447,237 A * | 9/1995 | Carter et al. | ................... | 206/570 |
| D657,054 S * | 4/2012 | Bacon | ......................... | D24/128 |
| 2004/0262867 A1* | 12/2004 | Arceta et al. | ............... | 280/47.35 |
| 2005/0159784 A1* | 7/2005 | Arceta | ........................... | 607/20 |

* cited by examiner

*Primary Examiner* — Mickey Yu
*Assistant Examiner* — Kaushikkumar Desai
(74) *Attorney, Agent, or Firm* — Peter Loffler (57) ABSTRACT

A medical organizer provides a professional, such as an anesthetist, quick access to the various items needed during a medical procedure without the need to turn away from the procedure. The organizer is formed of main housing that stabilizes various lines, such as circuit lines, IV lines, suction line etc., and also holds narcotics locked until needed. A secondary housing is removably held within the main housing and holds various implements such as catheters, swabs, alcohol, syringes and vials, waste receptacles, gauze, etc. The main housing can be secured to an IV post or operating room bed rail with the secondary housing held therein, or the secondary housing can be deployed and secured separately.

25 Claims, 10 Drawing Sheets

MEDICAL ORGANIZER

BACKGROUND OF THE INVENTION

1. Field of the Invention

The present invention relates to an organization system that is used by an anesthetist or other medical professional wherein the system has numerous compartments and other holding implements that are used by the profession during an operation or other procedure, the present invention keeping the various implements organized for easy access by the professional while maintaining stability in an unobtrusive fashion.

2. Background of the Prior Art

Many people believe that an anesthesiologist simply puts a person to sleep prior to an operation and thereafter allows the person to awaken following the procedure. If the job were that easy, then there would be no need for multiple years of residency and training after a doctor graduates from medical school. However, anesthesiologists are perioperative physicians who are tasked with a wide range of duties before, during, and after a procedure is performed on a patient, either in an operating room or other locale.

While the safe administration of anesthesia to a patient is central to an anesthesiologist's job, the job is much more complex than the untrained eye might see. Part of an anesthesiologist's duties include a preoperative medical evaluation of the patient prior to surgery, including an evaluation of the patient's medical history and current medical condition, the age of the patient, the procedure to be performed, any allergies of the patient, etc., consultation with the surgical team, creating and implementing a plan for the anesthesia tailored to the patient, airway management, intraoperative life support and provision of pain control, and proper post-operative management of the patient. The doctor (or other medical professional), must obtain the drugs to be used during the procedure prior to the procedure and must safe-keep the drugs (yes, theft does occur even in hospitals, with this requirement being per JCHAO mandates), must compound and dose the drugs, and must administer the drugs both prior to the commencement of the procedure, during the procedure itself, and after the procedure has ended. The anesthetist must be ready to administer additional or different drugs if the current drugs combination is not performing satisfactorily, or if the nature of the procedure suddenly changes, for example, a procedure performed under local anesthesia changes to one whether the patient must be quickly put asleep. During the procedure, the anesthetist is tasked with monitoring various signs of the patient, such as blood pressure, heart beat rate, oxygenation and carbon dioxide levels of the patient, etc., not only to be certain that the drugs being administered are performing satisfactorily, but also to give other doctors feedback which may be useful to these other doctors. Sometimes, the anesthetist needs to draw blood or other bodily fluids from the patient, either to help with the monitoring process, or for follow-up care subsequent to the procedure then being performed. Sometimes the anesthetist is required to perform other procedures around the medical building like intubations, placing IVs, arterial catheters and central line catheters.

These and other tasks make the day of an anesthetist, busy if not hectic. One thing that is evident, is the fact that the anesthetist requires different hardware in the operating room or other point of procedure location. Such items include the drugs to be used, syringes and vials including tape, alcohol, bandages, betadine swabs, IV and arterial catheters, laryngoscopes, endotracheal tubes, etc. Additionally, appropriate disposal receptacles tend to be located centrally, some distance away from the provider. Keeping these items organized and orderly tends to pose a challenge to the anesthetist. In addition to keeping the tools of the trade organized, the anesthetist must also know where the all the hardware for the case is located. While the operating room may be relatively large, the working space assigned to the anesthesiologist is relatively limited. The anesthetist must set up and be able to perform under all circumstances in the assigned space. In the event of an emergency, when seconds count, the anesthetist must be able to get the right tools to the right location without delay. While fumbling around for a pen in an office setting is innocent enough, in an operating room when the surgeon suddenly finds the need to put the patient to sleep to perform an unexpected cut, the anesthetist must be able to perform on the spot and without interfering with the other professionals involved in the procedure. This makes organization of the various tools of the anesthetist critical.

The current accepted methodology is to keep the needed items within the multitude of drawers within a centrally located cart and obtain each tool as needed therefrom. Many times one can find the provider fumbling through many drawers looking for exactly what that person needs, especially in an emergency situation. When the items are found, they can be placed in odd places, including the patient's chest, the cart behind the provider and elsewhere.

What is needed is a device that allows an anesthetist to be able to carry and organize the various tools that are needed or might be needed for a procedure, which gives the professional rapid and easy access to any tool that might be required at any given time. Such a device must be compact in design in order to allow the anesthetist to be able to use the device in a relatively compact work space, yet must be able to carry all of the tools that are needed by the anesthetist, all the while being able to carry the device from one work location to another. Such a device must be logically laid out so that the anesthetist can get whatever he or she needs in a moment's notice. Ideally, such a device should be of relatively simple design and construction.

SUMMARY OF THE INVENTION

The medical organizer of the present invention addresses the aforementioned needs in the art by providing an organizer that is used by an anesthetist (anesthesiologist, nurse anesthetist, or other anesthesia professional). The medical organizer is a relatively compact device that keeps order during a procedure all the while quickly and easily fitting into the available work space of the professional within close proximity to the professional at the same level/height as the target zone of the procedure. The medical organizer gives the professional rapid access to all key items that may be needed for executing the procedure efficiently. The medical organizer is portable so that is may be carried and used anywhere around the hospital, wherever a procedure must be performed, and it's elegance rests in its simplicity for ensuring it contains what is needed at hand in order to execute the procedure without the need to leave the work site. The medical organizer carries all of the supplies needed by the anesthetist, including having the ability to lock narcotics, and also helps stabilize the anesthesia circuit and IV infusion lines as needed by the anesthetist, and also provides for easy and proper disposal of the various items of waste generated during the procedure without the anesthetist turning away from the procedure. It also serves as a transport unit that carries all necessary including emergency items that may be necessary during transport of a critically ill patient. The medical organizer is of relatively simple design and construction, being made using standard manufacturing techniques.

The medical organizer of the present invention is comprised of a generally rectangular main housing that has a first base, a plurality of first walls extending upwardly from the first base, and a lid hingedly attached to one of the first walls, such that the lid is capable of closing the main housing, the lid having a lockable compartment, and such that one of the first walls is hingedly attached to the first base. A first telescoping line stabilizer is rotatably attached to one of the first walls, the first line stabilizer having at least one notch extending diagonally inwardly from a side edge of the first line stabilizer. A second telescoping line stabilizer is also rotatably attached to one of the first walls, the second line stabilizer having a wire line stabilizer located on a top thereof. A channel clamp that has a first channel is rotatably attached to one of the first walls, the channel clamp having a lock threadably attached thereto for frictionally locking the channel clamp. A generally rectangular shaped secondary housing has a second base and a plurality of second walls extending upwardly from the second base, the secondary housing being removably receivable within the main housing, such that the secondary housing is segregated into a plurality of compartments. A tray is rotatably attached to the secondary housing such that the tray is capable of overlying one of the compartments. A stabilizer base has a second channel and is attached to a lower surface of the second base. A spring loaded clamp arm extends upwardly from the first base. A suction line clamp is attached to one of the first walls. A first arm is rotatably attached to the lid while a second arm is rotatably attached to one of the first walls such that the first arm and the second arm are capable of being rotated so as to be generally coextensive. A clamp stabilizer may be removably received within the first channel of the channel clamp. A hook rotatably attached to one of the first walls. A spool holder is disposed within the secondary housing while a cutting blade is attached to one of the second walls proximate a top thereof. A bin is removably receivable within one of the compartments. A plate disposed within the secondary housing and is generally parallel with the base, the plate having a plurality of openings. A plurality of baffles is disposed within one of the compartments. A band is attached to the secondary housing such that the band forms an open pocket with an outer surface of one of the second walls.

BRIEF DESCRIPTION OF THE DRAWINGS

Similar reference numerals refer to similar parts throughout the several views of the drawings.

DESCRIPTION OF THE PREFERRED EMBODIMENT

Figure 1:
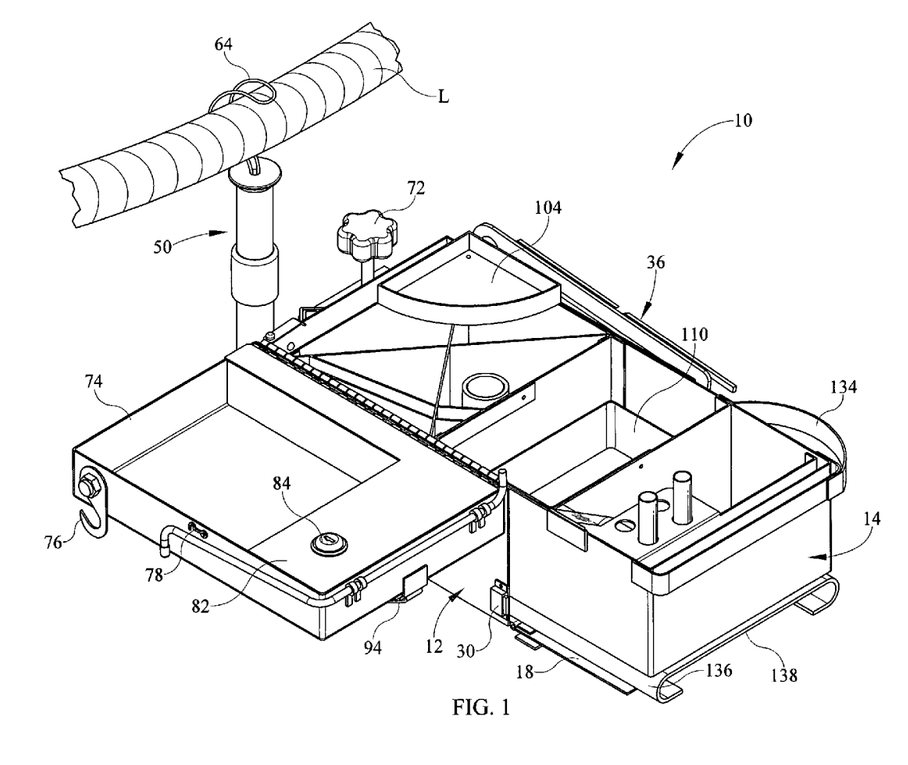
FIG. 1 is a perspective view of the medical organizer of the present invention holding various items therein including an anesthesia circuit holder.
Figure 2:
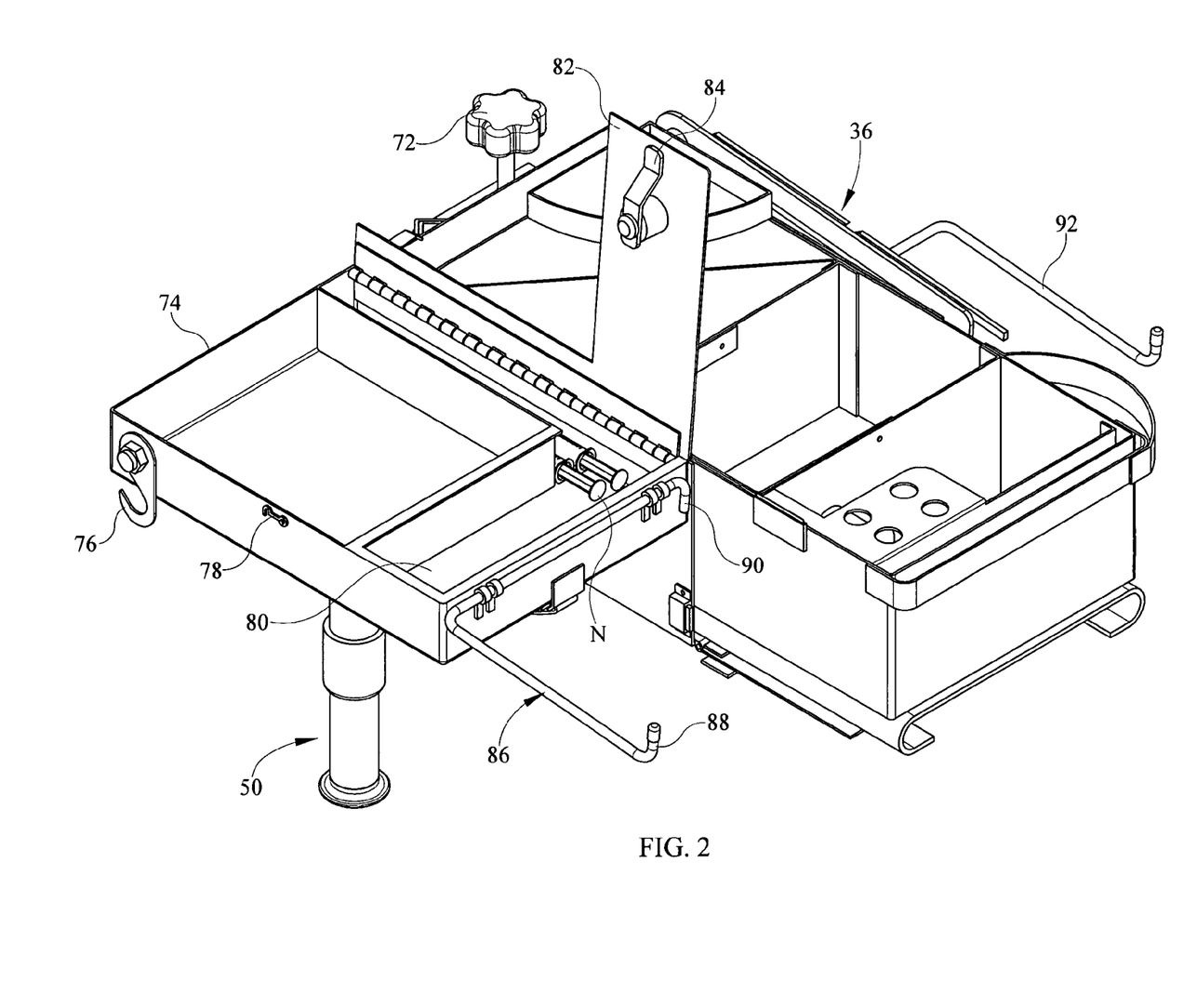
FIG. 2 is a perspective view of the medical organizer illustrating access to the locked narcotics holding area and with the garbage bag holding arms deployed.
Figure 3:
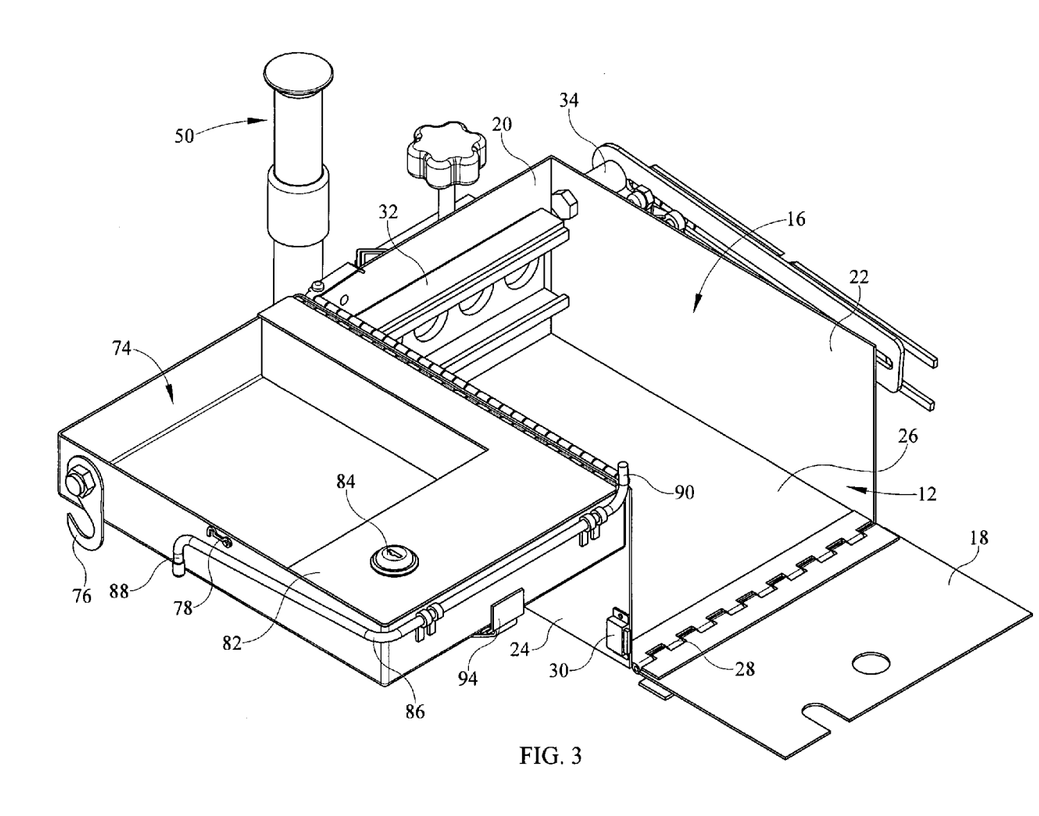
FIG. 3 is a perspective view of the main housing unit of the medical organizer.
Figure 4:
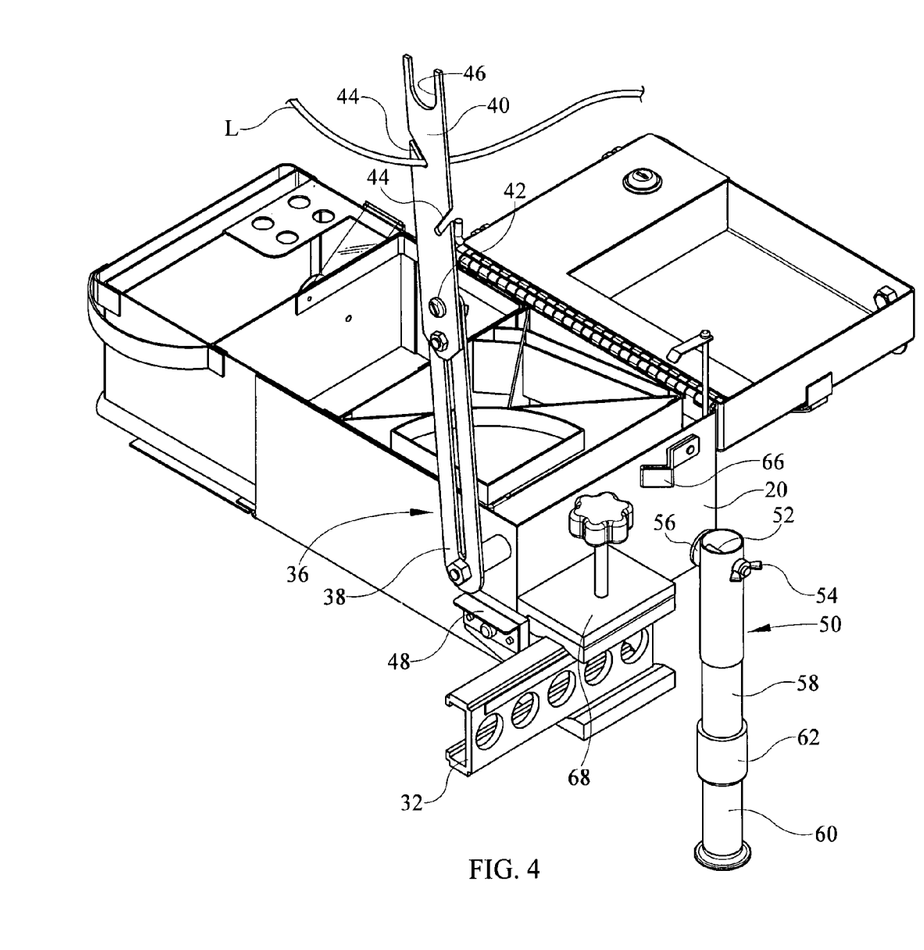
FIG. 4 is a perspective view of the medical organizer holding a line and using the clamp extender.
Figure 5:
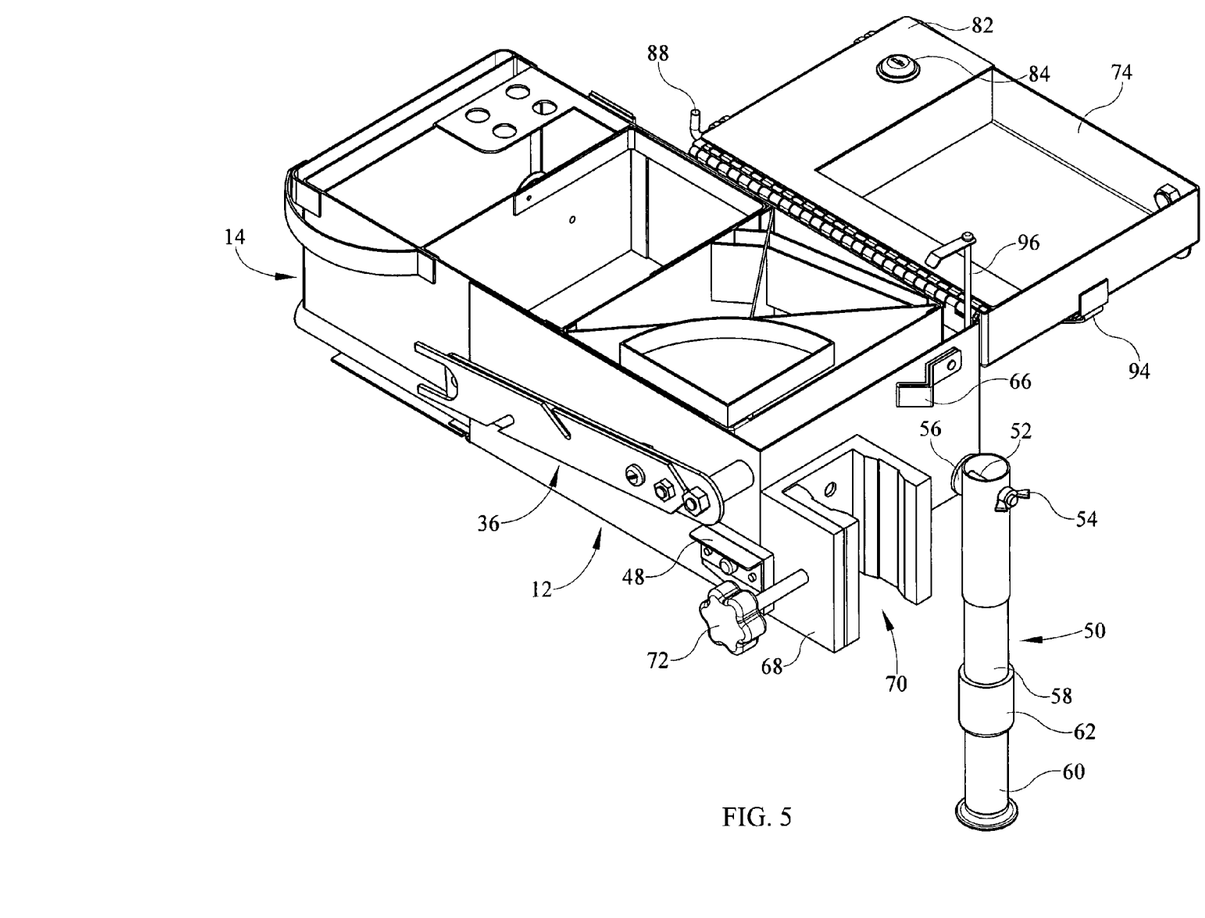
FIG. 5 is a rotated perspective view of the medical organizer
Figure 6:
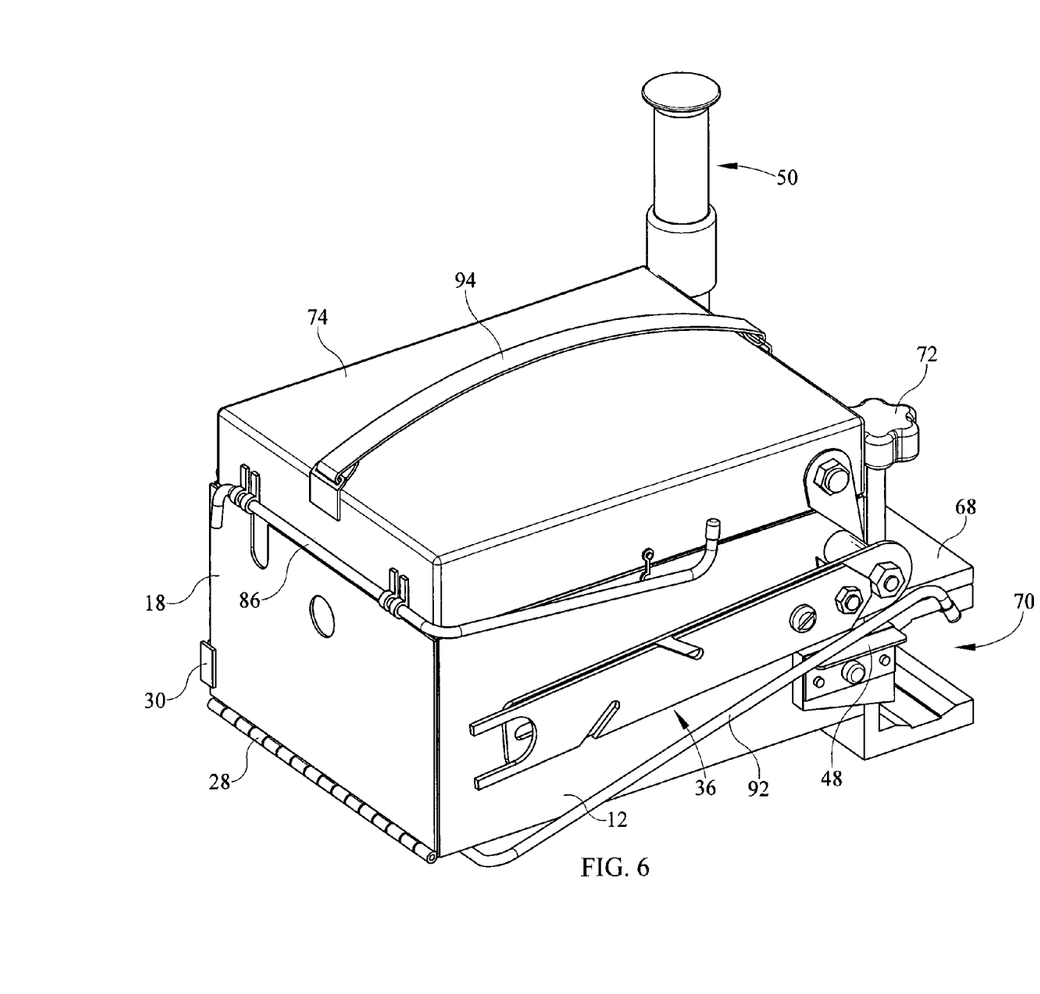
FIG. 6 is a perspective view of the main housing of medical organizer in a compacted position ready for transport.
Figure 7:
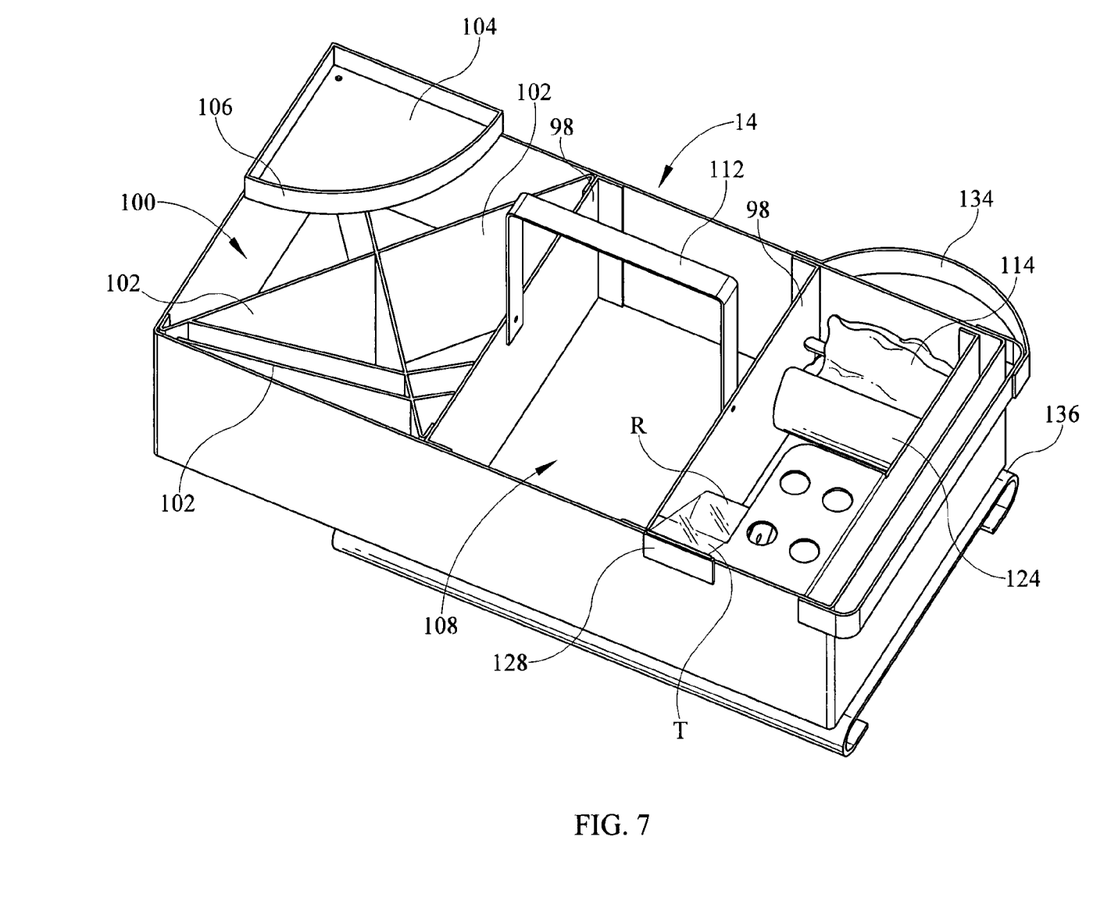
FIG. 7 is a perspective view of the secondary housing unit of the medical organizer.
Figure 8:
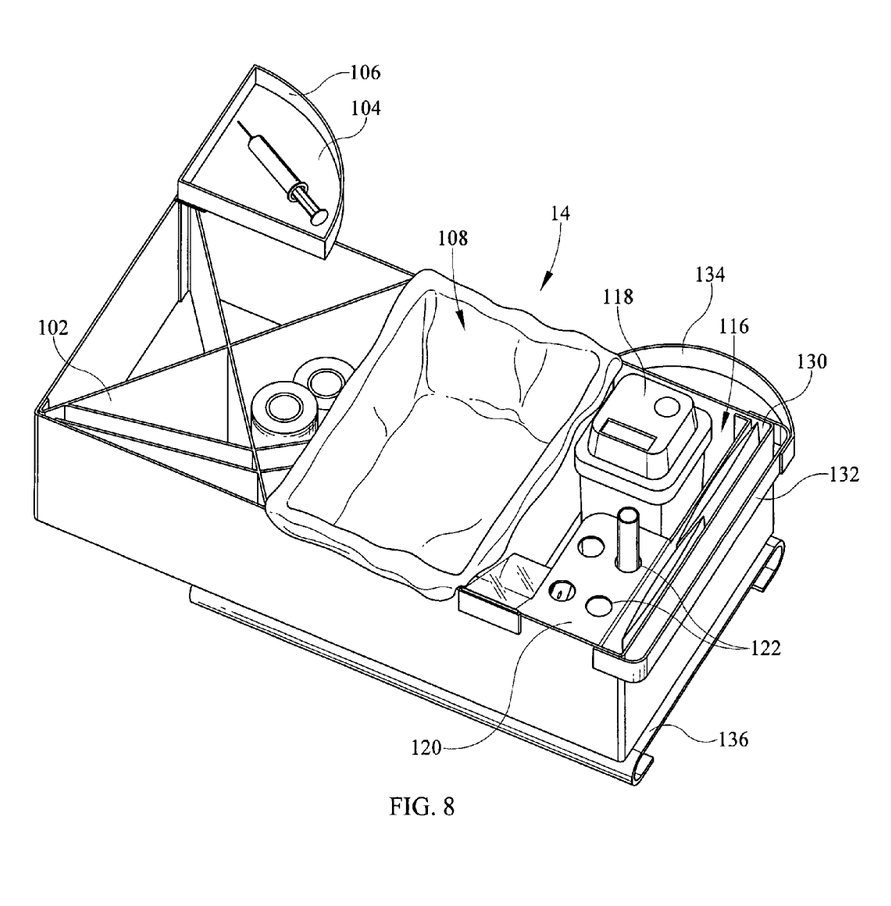
FIG. 8 is a perspective view of the secondary housing unit of the medical organizer stocked and ready for performance.
Figure 9:
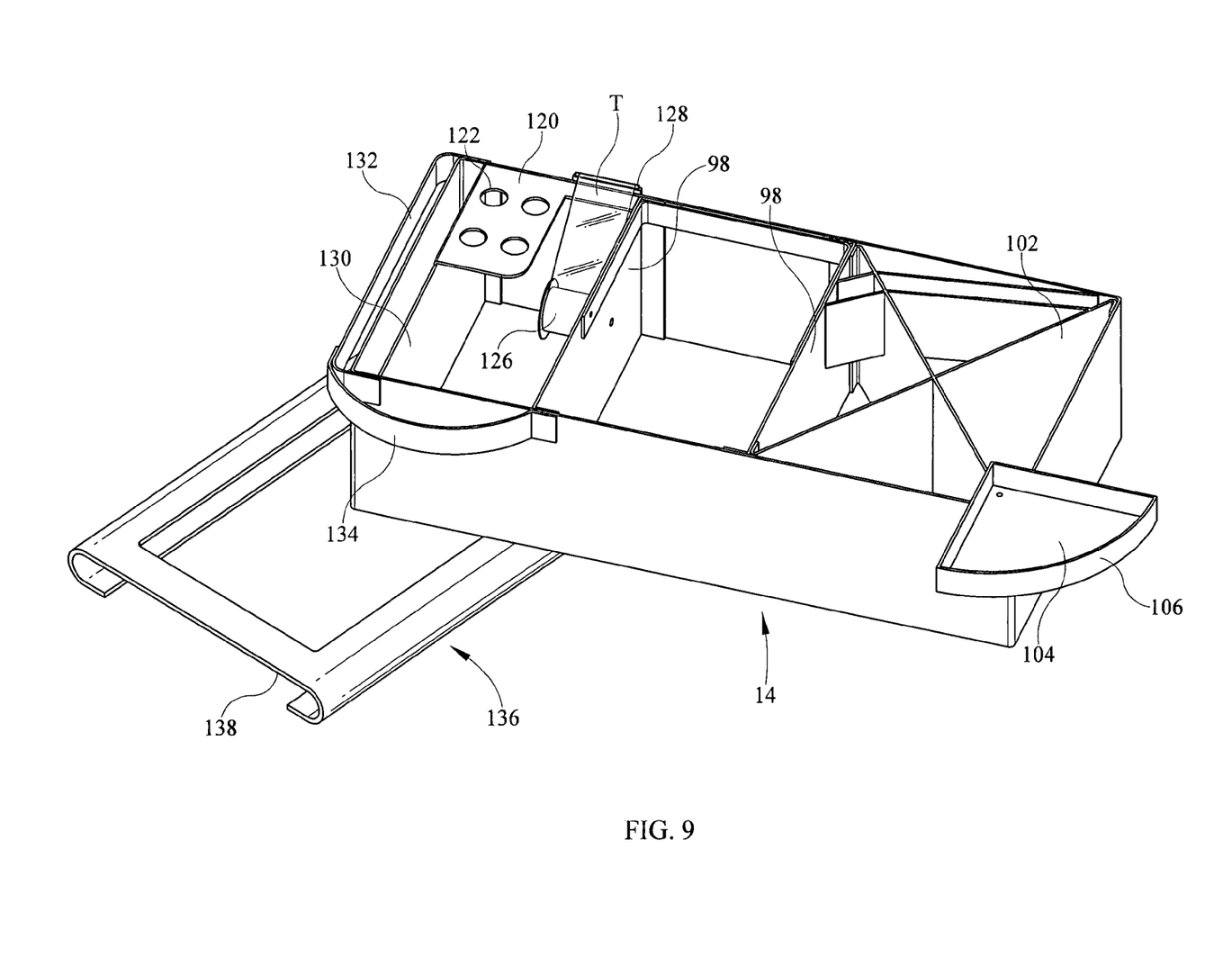
FIG. 9 is a perspective view of the secondary housing unit of the medical organizer in rotated relation with its stabilizer base.
Figure 10:
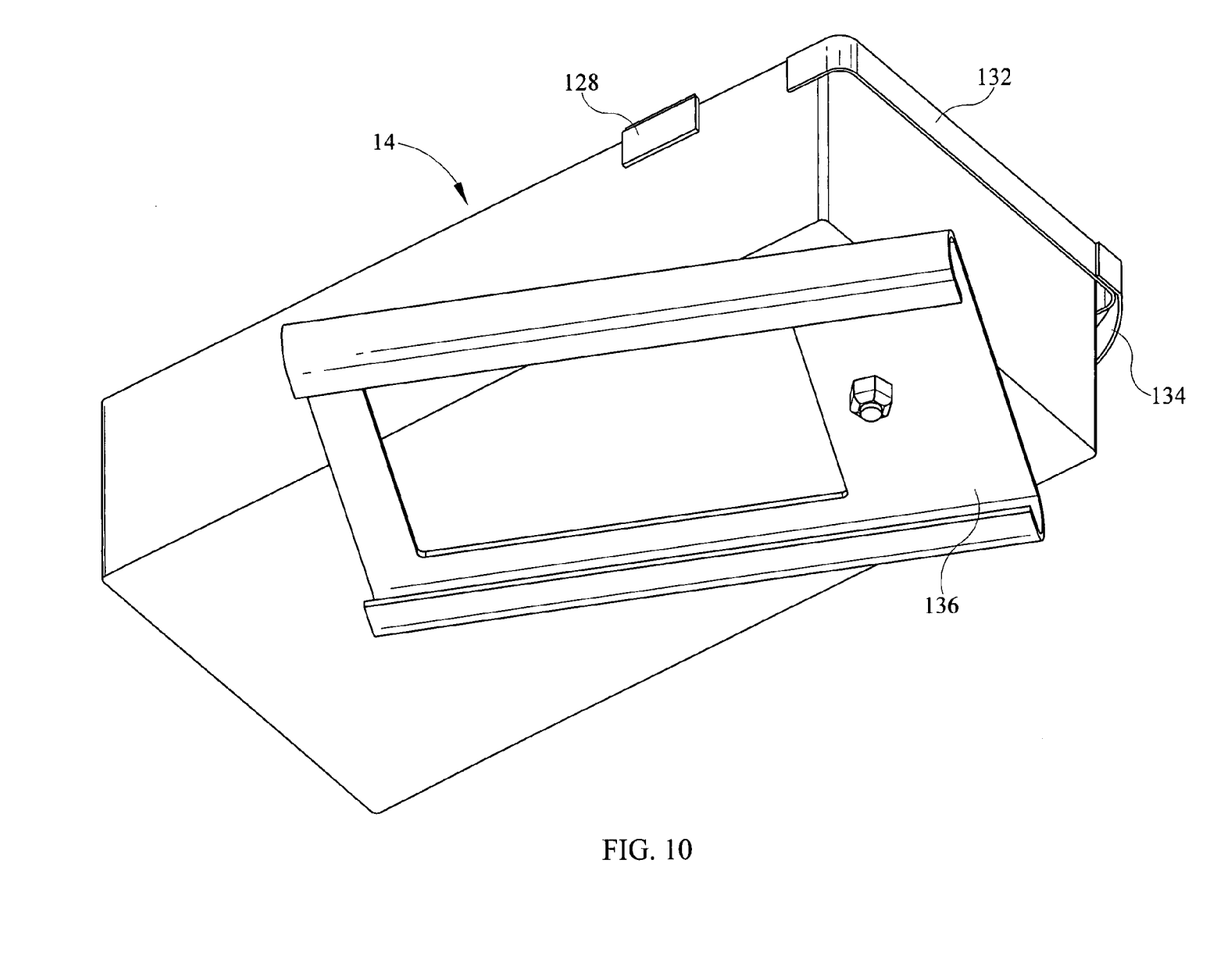
FIG. 10 is an underside perspective view of the secondary housing unit of the medical organizer.

Referring now to the drawings, it is seen that the medical organizer of the present invention, generally denoted by reference numeral 10, is comprised of a main housing 12 and a secondary housing 14 that is removably received within the main housing 12. As seen, the main housing 12 is a generally rectangular shaped body member that has an internal cavity 16 for holding the secondary housing 14, and having a first side 18 and an opposing second side 20, joined by a third side 22 and an opposing fourth side 24 all depending upwardly from a bottom 26. The first side 18 of the main housing 12 is attached to the bottom 26 via an appropriate hinge member 28 in order to allow this side 18 to drop down as needed. A latch system 30 of any appropriate design (magnetic, mechanical, etc.,) is used to hold this side 18 in an upright closed position when drop down is not needed. Removably attached to an inner surface of the opposing second side 20 of the main housing 12 within the internal cavity 16 is a clamp stabilizer 32. Removable attachment of the clamp stabilizer 32 to the side 20 is via any appropriate manner well known in the art, such as hooks, cooperating hook and loop material, etc., (none illustrated).

A post 34 extends outwardly from the third side 22 of the main housing 12. A first telescoping line holder/stabilizer 36, which is a generally flat plate member, is swively attached to the post 34 such that the first line holder 36 is comprised of a lower section 38 that is attached to the post 34 and an upper section 40 that is capable of telescoping with respect to the first section 38. An appropriate screw lock 42 is attached to the second section 40 in order to lock the second section 40 to the first section 38 at the desired height of telescope. As seen, the second section 40 has at least one diagonally disposed notch 44 located along its length, each notch 44 capable of removably receiving a line L (such as an intravenous infusion line, etc.,) therein. The top of the second section 40 also has a notch 46 thereat for receiving a line L therein. Also swively attached to this third side 22 of the main housing 12 is a stop 48.

A second telescoping line holder 50 is swively attached to the second side 20 of the main housing 12 via an appropriate screw 52, nut 54, and washer 56 system as is well known in the art. This second line holder 50 is a tubular member that has a first section 58 that is slidable with respect to a second section 60 such that a threaded lock knuckle 62 holds the second section 60 in position with respect to the first section 58. As seen, located on the end of the second section 60 of this second line holder 50 is a circuit line holder 64, which is a special wire based holder that resiliently receives the circuit line C therein. A suction line stabilizer 66 is attached to the second side 20 of the main housing 12. A channel clamp 68 is swively attached to the second side 20 of the main housing in spaced apart relation to both the second line holder 50 and the suction line stabilizer 66. The channel clamp 68 has a channel 70 therein to be received on an appropriate post, such as an IV post. A threaded lock 72 frictionally locks the channel clamp 68 onto the post, such as an IV post or the side rail of an operating room bed, while the stop 48 is used to hold the channel clamp 68 in position, either generally horizontally disposed or generally vertically disposed depending on the placement of the attachment of the channel clamp 68.

A lid 74 is hingedly attached to the fourth side 24 of the main housing 12 such that the lid 74 has a latch 78. A rotatably attached hook 76 is provided for line stabilization and hanging needed items such as EKG leads, oximeter leads, and blood pressure leads, etc. 74. A compartment 80 is located within the lid 74, which compartment 80 has its own lid 82 that is hingedly attached to the major lid 74 such that a lock 84 is provided for maintaining the compartment in a closed and locked orientation, access to the compartment 80 gained via unlocking of the lock 84 via the appropriate key (not illustrated). A securement arm 86 is rotatably attached to an edge of the major lid 74, this securement arm 86 having a first upwardly turned end 88 and a second downwardly turned end 90. A companion securement arm 92 is rotatably attached to the bottom 26 of the main housing 12. A carrying handle 94 is located on the major lid 74.

A spring-loaded clamp arm 96 extends upwardly from the bottom 26 of the main housing 12 proximate the intersection of the second side 20 and the fourth side 24.

The various components of the main housing 12 are made from an appropriate material, such as aluminum, hard plastic, etc., and may have an appropriate coating therein (powder coating, etc.,) for added durability.

As seen, the secondary housing 14 is also a generally rectangular shaped unit that is slidably and removably disposed within the internal cavity 16 of the main housing 12. The secondary housing 14, which has an open top, is segregated into three separate compartments via internal walls 98. The first compartment 100 of the secondary housing 14 has a series of internal baffles 102 in order to provide storage for various clean materials that may be used during a procedure such as gauze, alcohol swabs, tourniquets, tegaderms, claves, etc. A tray 104 is swivelly attached to a corner of the secondary housing 14 such that this tray 104 overlies a portion of the first compartment 100 of the secondary housing 14 in order to protect the contents within this first compartment 100 and also to serve as a work tray for placing hardware thereon, which hardware is going to be immediately needed during a procedure being performed. The tray 104 has lips 106 in order to help retain hardware therein as well as to serve other functions such as placement of tegaderm thereon.

The second compartment 108 is an open space designed for receiving various non-sharps waste therein. A removable bin 110 may be removably receivable within the second compartment 108 in order to receive the waste therein and be removable and replaceable. Alternatively, or in addition, a disposable liner 114 may be provided to line the second compartment 108 or its bin 110. A handle 112 is rotatably attached to the internal walls 98 such that the handle 112 straddles the second compartment.

The third compartment 116 has a sharps container 118 of any appropriate design held therein. Additionally, extending from one or more of the sidewalls of the secondary housing 14 (or from the internal wall) is a plate member 120 that has a series of openings 122 that hold various vials, tubes, syringes, needles, etc. Additionally, a garbage bag dispenser 124 is disposed underneath the plate member 120 such that the garbage bags 114 dispensed from the dispenser 124 pass through one of the openings 122 in order to line the second compartment 108 or bin 110 as described above. A spool 126 extends outwardly from the internal wall 98 (or sidewall of the secondary housing 14) such that a tape roll R is received thereon. As seen, a tape cutter 128 is located on the sidewall of the secondary housing 14 in order to provide cutting of the tape T from the tape roll R. A retainer compartment 130 extends between walls of the secondary housing 14, within the housing 14, in order to hold Arrow arterial catheters therein, while a retainer band 132 extends between the same walls of the secondary housing 14, exterior of the walls of the housing 14 and parallel with the retainer compartment 130 in order to retain many IV catheters, large draw tubes, endotracheal tubes, etc. An arterial wrist support band 134 is attached to an exterior surface of one of the walls of the secondary housing proximate the third compartment 116.

A stabilizer base 136 is swivelly attached to an underside of the secondary housing 14, the stabilizer base 136 having a channel 138, which channel 138 is capable of being sleeved onto a detachable arm rest (not illustrated) used on typical operating room tables.

Similar to the main housing 12, the various components of the secondary housing 14 are made from an appropriate material, such as aluminum, hard plastic, or combination thereof, etc., and may have an appropriate coating therein (powder coating, etc.,) for added durability.

In order to utilize the medical organized 10 of the present invention, the device 10 is populated with the various hardware implements needed. For example, narcotics N are loaded into the compartment 80 of the major lid 74 as needed, and the compartment 80 is locked via the lock 84. A sharps container 118 is loaded into the third compartment 116 of the secondary housing 14 as are a roll of tape R which is loaded onto the spool 126 with the tape end T preloaded onto the cutter 128. A garbage bag roll 114 is preloaded underneath the plate 120 and then a bag 114 pulled through an opening 122 for preloading. Additional implements are loaded into the secondary housing (catheters, gauze, vials, swabs, etc., as described infra) as can be expected to be used in the procedure at hand. If not already so, the secondary housing 14 is slid into the internal cavity 16 of the main housing 12. The major lid 74 is closed and latched as appropriate. The anesthetist can carry the device 10 to the location to be performed via the handle 94. At the procedure location, the professional attaches the main housing 12 to an appropriate post via the channel clamp 68, the channel clamp 68 rotated so that its channel 70 aligns with the longitudinal axis of the post to which the channel clamp 68 is to be attached. Once the channel clamp 68 is rotated to its desired position, the stop 48 is rotated so as to be deployed in order to prevent further rotation of the channel clamp 68. The threaded lock 72 is appropriately rotated so as to frictionally lock the channel clamp 68 to the post. If needed or desired, either for space limitations or for convenience, the clamp adapter 32 is locked within the channel 70 of the channel clamp 68 via the threaded lock 72 and the clamp adapter 32 is sleeved onto the desired target surface.

The major lid 74 is unlatched and opened. Whenever needed, the lock 84 is unlocked so as to gain access to the narcotics N held within the compartment 80 for appropriate deployment of the narcotics N. The remainder of the inside surface of the major lid (the area outside of the compartment 80, may be used as a work surface.

Both the first telescopic line holder 36 and the second telescopic line holder 50 are rotated into their respective desired positions and are extended to their respective desired heights and locked thereinto. The various lines L are attached as needed and stabilized thereby. The securement arm 86 is rotated so as to extend outwardly from the major lid 74 so that its first turned end 88 extends upwardly and the second turned end 90 extends downwardly and lies generally flush against a side of the major lid 74 in order to prevent further turning of the extension arm 86. The companion extension arm 92 is also deployed so as to be essentially coextensive with the first extension arm 86. A garbage bag 114 is secured to the first extension arm 86 and the second extension arm 92. The device 10 is now ready for use, with the various hardware implements needed by the anesthetist organized and ready for retrieval. Disposal of waste is also easy either into the garbage bag 114, into the second compartment 108, either directly or into the removable bin 110, or into the sharps container 116 as appropriate. The various lines L are stabilized and organized. The suction line stabilizer 66 secures the stiction line in a ready to use position, while the spring loaded clamp arm 86 is also used as needed, either to clamp down/stabilize a central line catherization kit.

If needed, the secondary housing 14 is detached from the main housing 12 by sliding the secondary housing 14 out of the internal cavity 16 of the main housing 12 and placed onto the arm rest thereby all items needed for arterial catheter placement or IV placement are right where they are needed. If the main housing 12 is to be further used by the anesthetist, the first side 18 may be closed and latched with the major lid 74 similarly closed and latched for transport. The first telescopic line holder 36 and the second telescopic line holder 50 are maintained in position if the main housing 12 is being used during an active procedure while separated from the secondary housing 14.

Similarly, the secondary housing 14 may be separated from the main housing 12, either for convenience at the work site or for necessity, by sliding the secondary housing 14 out from the main housing 12. As such, the secondary housing 14 may be a standalone organizer holding the various hardware implements needed by the anesthetist minus the line holders and clamps. If needed, the secondary housing 14 is sleeved onto the detachable arm rest of an operating room or other similar surface as needed.

While the invention has been particularly shown and described with reference to an embodiment thereof, it will be appreciated by those skilled in the art that various changes in form and detail may be made without departing from the spirit and scope of the invention.

I claim:

1. An organizer comprising:
   a main housing having a first base, a plurality of first walls extending upwardly from the first base, and a lid hingedly attached to one of the first walls, such that the lid is capable of closing the main housing, the lid having a lockable compartment;
   a first line stabilizer rotatably attached to one of the first walls, the first line stabilizer having a notch extending diagonally inwardly from a side edge of the first line stabilizer;
   a second line stabilizer rotatably attached to one of the first walls, the second line stabilizer having a wire line stabilizer located on a top thereof;
   a channel clamp having a first channel, the channel clamp rotatably attached to one of the first walls, the channel clamp having a lock threadably attached thereto for frictionally locking the channel clamp; and
   a shaped secondary housing having a second base and a plurality of second walls extending upwardly from the second base, the secondary housing removably receivable within the main housing, such that the secondary housing is segregated into a plurality of compartments.

2. The organizer as in claim 1 wherein the first line stabilizer and the second line stabilizer are each telescoping.

3. The organizer as in claim 1 further compromising a spring loaded clamp arm extending upwardly from the first base.

4. The organizer as in claim 1 further comprising a suction clamp attached to one of the first walls.

5. The organizer as in claim 1 further comprising:
   a first arm rotatably attached to the lid; and
   a second arm rotatably attached to one of the first walls such that the first arm and the second arm are capable of being rotated so as to be generally coextensive.

6. The organizer as in claim 1 further comprising a hook rotatably attached to one of the first walls.

7. The organizer as in claim 1 wherein one of the first walls is hingedly attached to the first base.

8. The organizer as in claim 1 further comprising a tray rotatably attached to the secondary housing such that the tray is capable of overlying one of the compartments.

9. The organizer as in claim 1 further comprising:
   a spool holder disposed within the secondary housing: and
   a cutter attached to one of the second walls proximate a top thereof.

10. The organizer as in claim 1 further comprising a bin removably receivable within one of the compartments.

11. The organizer as in claim 1 further comprising a plate disposed within the secondary housing, generally parallel with the base, the plate having a plurality of openings.

12. The organizer as in claim 1 further comprising a stabilizer base having a second channel, the stabilizer base rotatably attached to a lower surface of the second base.

13. The organizer as in claim 1 further comprising a plurality of baffles disposed within one of the compartments.

14. The organizer as in claim 1 further comprising a band attached to the secondary housing, such that the band forms an open pocket with an outer surface of one of the second walls.

15. An organizer comprising:
   a main housing having a first base, a plurality of first walls extending upwardly from the first base, and a lid hingedly attached to one of the first walls, such that the lid is capable of closing the main housing, the lid having a lockable compartment;
   a first telescoping line stabilizer rotatably attached to one of the first walls, the first line stabilizer having a notch extending diagonally inwardly from a side edge of the first line stabilizer;
   a second telescoping line stabilizer rotatably attached to one of the first walls, the second line stabilizer having a wire line stabilizer located on a top thereof;
   a channel clamp having a first channel, the channel clamp rotatably attached to one of the first walls, the channel clamp having a lock threadably attached thereto for frictionally locking the channel clamp;
   a shaped secondary housing having a second base and a plurality of second walls extending upwardly from the second base, the secondary housing removably receivable within the main housing, such that the secondary housing is segregated into a plurality of compartments;
   a tray rotatably attached to the secondary housing such that the tray is capable of overlying one of the compartments; and
   a stabilizer base having a second channel, the stabilizer base rotatably attached to a lower surface of the second base.

16. The organizer as in claim 15 further compromising a spring loaded clamp arm extending upwardly from the first base.

17. The organizer as in claim 16 further comprising a suction clamp attached to one of the first walls.

18. The organizer as in claim 17 further comprising:
   a first arm rotatably attached to the lid; and a second arm rotatably attached to one of the first walls such that the first arm and the second arm are capable of being rotated so as to be generally coextensive.

19. The organizer as in claim 15 further comprising a hook rotatably attached to one of the first walls.

20. The organizer as in claim 19 wherein one of the first walls is hingedly attached to the first base.

21. The organizer as in claim 20 further comprising:

a spool holder disposed within the secondary housing: and a cutter attached to one of the second walls proximate a top thereof.

22. The organizer as in claim 21 further comprising a bin removably receivable within one of the compartments.

23. The organizer as in claim 22 further comprising a plate disposed within the secondary housing, generally parallel with the base, the plate having a plurality of openings.

24. The organizer as in claim 23 further comprising a plurality of baffles disposed within one of the compartments.

25. The organizer as in claim 24 further comprising a band attached to the secondary housing, such that the band forms an open pocket with an outer surface of one of the second walls.

* * * * *